United States Patent
Deshpande

(10) Patent No.: US 7,702,600 B2
(45) Date of Patent: Apr. 20, 2010

(54) SYSTEMS AND METHODS FOR CLINICAL DECISION CRAWLER AGENT

(75) Inventor: Shrikant L. Deshpande, Glendale Heights, IL (US)

(73) Assignee: General Electric Company, Schenectady, NY (US)

( * ) Notice: Subject to any disclaimer, the term of this patent is extended or adjusted under 35 U.S.C. 154(b) by 284 days.

(21) Appl. No.: 11/389,857

(22) Filed: Mar. 27, 2006

(65) Prior Publication Data

US 2007/0226167 A1 Sep. 27, 2007

(51) Int. Cl.
*G06N 5/00* (2006.01)

(52) U.S. Cl. .................................................... 706/45
(58) Field of Classification Search ............... 706/45
See application file for complete search history.

(56) References Cited

U.S. PATENT DOCUMENTS

| | | | |
|---|---|---|---|
| 7,230,529 B2* | 6/2007 | Ketcherside et al. ... | 340/539.12 |
| 2004/0078224 A1* | 4/2004 | Schramm-Apple et al. ..... | 705/2 |
| 2004/0122702 A1* | 6/2004 | Sabol et al. ..................... | 705/2 |
| 2004/0122709 A1* | 6/2004 | Avinash et al. .................. | 705/2 |
| 2004/0143462 A1* | 7/2004 | Hunt et al. ...................... | 705/3 |
| 2007/0061393 A1* | 3/2007 | Moore .......................... | 709/201 |
| 2007/0134672 A1* | 6/2007 | Choi et al. ...................... | 435/6 |

OTHER PUBLICATIONS

Mikhail Simonov et al. "Information, Knowledge and Interoperability for Healthcare Domain", Proceedings of the First International Conference on Automated Production of Cross Media Content for Multi-Channel Distribution (AXMEDIS'05).*
AXMEDIS call for paper, Nov. 30-Dec. 2, 2005, Florence Italy.*
Chen et al.; "HelpfulMed: Intelligent Searching for Medical Information"; Journal of the American Society for Information Science and Technology; Jun. 7, 2003; pp. 683-694.*
Dong; "Enhanced Quality and Quantitiy of retrieval of Critially Appraised Topics using the CAT Crawler"; Informatics for Health and Social Care; Mar. 1, 2004, pp. 43-55.*
Dong; "Qantitative Evaluation of recal and precision of CAT Crawler, a search engine specialized on retrieval of Critically Appraised Topics"; PubMed Central; Dec. 10, 2004, pp. 1-7.*

(Continued)

*Primary Examiner*—David R Vincent
*Assistant Examiner*—Lut Wong
(74) *Attorney, Agent, or Firm*—McAndrews, Held & Malloy, Ltd.; Peter J. Vogel; Michael A. Dellapenna

(57) ABSTRACT

Certain embodiments of the present invention provide a system for clinical decision support including a crawler agent component. The crawler agent component is adapted to receive a search parameter. The search parameter specifies a criteria for evidence data to be searched for. The crawler agent component is adapted to initiate a search of a plurality of evidence sources based at least in part on the search parameter. The search identifies the evidence data. The evidence data is utilized by the clinical decision support system to provide decision support to a healthcare provider for a patient.

12 Claims, 2 Drawing Sheets

OTHER PUBLICATIONS

Adhikari et al., Medical Informatics in the Intensive care Unit: Overview of Technology Assessment, Mar. 2003, pp. 41-47.*
Jahnke-Weber, Jens H, et al., Making available Clinical Decision Support in Service-Oriented Architectures, 2007.*
Bidwell "Finding the evidence: resources and skill for locating information on clinical effectiveness" 2004.*
Dong; Enhanced quality and . . . ; Informatics for Health and Social Care; Mar. 2004.
Chen; HelpfulMed: Intelligent searching . . . ; ASIST Journal; Jun. 2003.
Dong; Quantitative evaluation . . . ; PubMed Central; Dec. 2004.

* cited by examiner

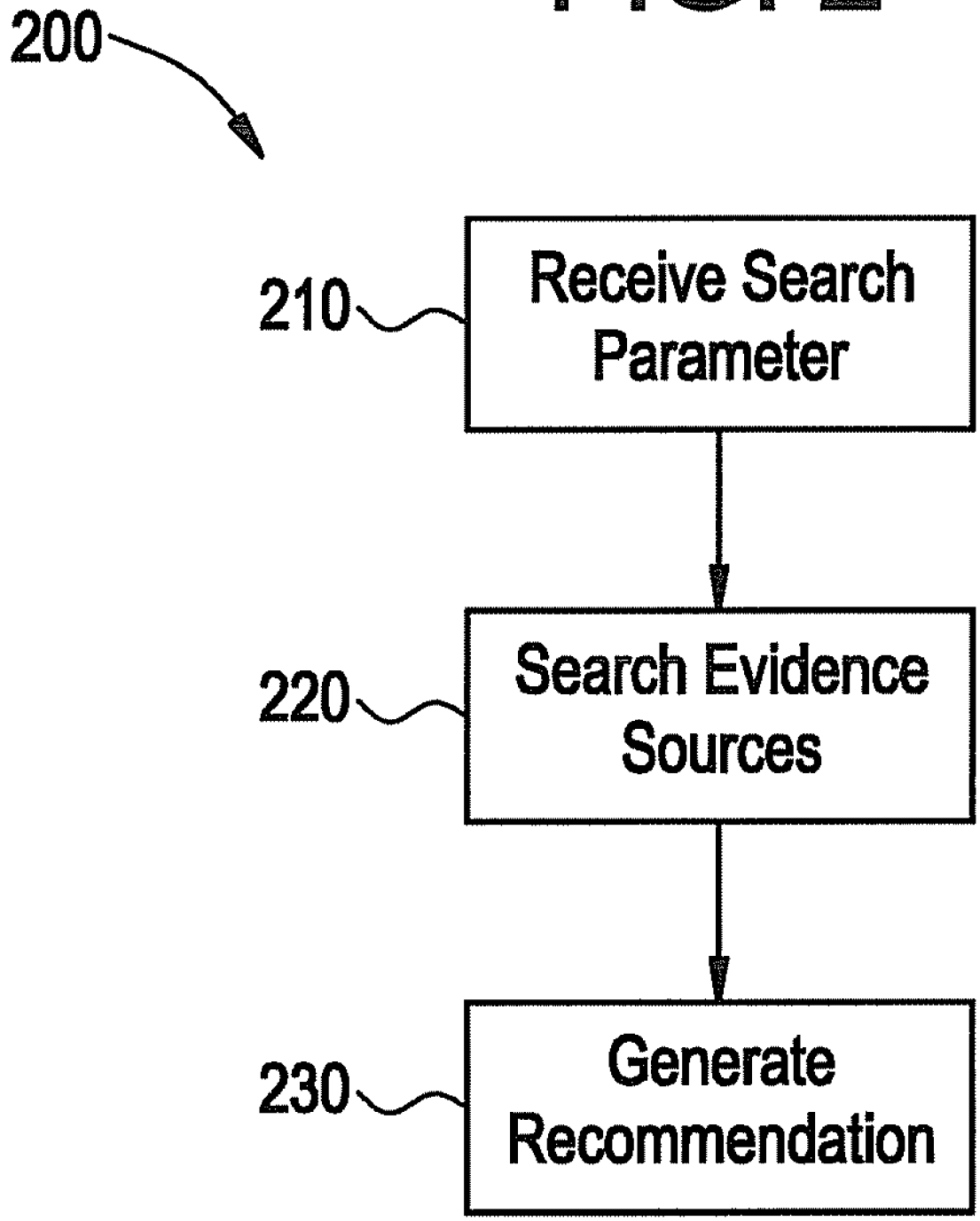

SYSTEMS AND METHODS FOR CLINICAL DECISION CRAWLER AGENT

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to clinical decision support. More particularly, the presently described technology relates to systems and methods for a clinical decision support crawler agent.

Healthcare facilities, such as hospitals or clinics, include medical information management systems, such as hospital information systems (HIS), radiology information systems (RIS), clinical information systems (CIS), cardiovascular information systems (CVIS), picture archiving and communication systems (PACS), laboratory information systems (LIS), and electronic medical records (EMR). Information stored may include patient medical histories, imaging data, test results, diagnosis information, management information, and/or scheduling information, for example. The information may be centrally stored or divided at a plurality of locations.

One example of a medical information management system is a PACS. PACS connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining healthcare operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

A reading, such as a radiology or cardiology procedure reading, is a process of a healthcare practitioner, such as a radiologist or a cardiologist, viewing digital images of a patient. The practitioner performs a diagnosis based on the content of the diagnostic images and reports on the results electronically (e.g., using dictation or otherwise) or on paper. The practitioner typically uses other evidence to aid in performing the diagnosis. Some examples of other evidence are prior (e.g., historical) exams and their results, other images, key image notes, laboratory exams and reports (such as blood work), allergies, pathology results, medication, alerts, document images, and other reports. In addition, the practitioner may want to consider other clinical evidence relevant to the context of the diagnosis being made as well as evidence pertaining to family members that may have a genetic link to the patient.

However, with current systems, the healthcare practitioner must manually seek out any additional evidence to be used in performing the diagnosis. That is, current systems do not automatically provide the practitioner with additional, potentially relevant, evidence to be considered.

In addition, relevant evidence may be located in various evidence sources. Evidences sources may include, for example, medical information management systems in different healthcare facilities. The healthcare facilities, such as hospitals and clinics, may be geographically distributed, and potentially even in different countries. For example, a patient may have gone to a hospital while on vacation years prior and had x-rays taken that might be relevant evidence for a healthcare practitioner to consider in making the current diagnosis. As another example, a patient may visit another geographic location or country for a special medical procedure, perhaps for cost or clinical reasons. As another example, a patient may have moved or immigrated from another city, region, state, or country. Current systems do not provide an efficient mechanism to gather evidence from evidence sources such as remote facilities, hospitals, or clinics. That is, current systems do not allow a practitioner to easily access such evidence.

Further, in addition to difficulty in obtaining the evidence, a practitioner must know of the existence of the evidence and where it is located. It is virtually impossible for a practitioner to manually search every possible healthcare facility's medical information management systems to locate potentially relevant evidence. A healthcare practitioner cannot obtain and utilize evidence he does not know about.

Clinical decision support systems provide assistance to healthcare providers such as physicians. A clinical decision support system may be part of a CIS, HIS, and/or PACS, for example. For example, a clinical decision support system in a PACS can aid a physician in making decisions regarding diagnosis and/or treatment. A clinical decision support system is particularly useful for aiding a healthcare practitioner in situations beyond the context of the practitioner's experience. A clinical decision support system may provide a recommendation for diagnosis and/or treatment. The recommendation may be based on one or more pieces of evidence provided to the clinical decision support system. As is true for a healthcare provider, a clinical decision support system can provide a better recommendation when more evidence is available to be considered.

Thus, there is a need for a healthcare practitioner to be able to locate and obtain access to evidence from multiple evidence sources. Further, there is a need for a clinical decision crawler agent to aid the practitioner to locate and obtain evidence for diagnosis and/or treatment and to make a recommendation based on the obtained evidence.

BRIEF SUMMARY OF THE INVENTION

Certain embodiments of the present invention provide a system for clinical decision support including a crawler agent component. The crawler agent component is adapted to receive a search parameter. The search parameter specifies a criteria for evidence data to be searched for. The crawler agent component is adapted to initiate a search of a plurality of evidence sources based at least in part on the search parameter. The search identifies the evidence data. The evidence data is utilized by the clinical decision support system to provide decision support to a healthcare provider for a patient.

Certain embodiments of the present invention provide a method for clinical decision support including receiving a search parameter and searching of a plurality of evidence sources. The search parameter is received at a crawler agent component. The search parameter specifies a criteria for evidence data to be searched for. The search is based at least in part on the search parameter. The search identifies the evidence data. The evidence data is utilized by a clinical decision support system to provide decision support to a healthcare provider for a patient.

Certain embodiments of the present invention provide a computer-readable medium including a set of instructions for execution on a computer, the set of instructions including a search parameter receiving routine and a search routine. The search parameter receiving routine is configured to receive a search parameter. The search parameter specifies a criteria for evidence data to be searched for. The search routine is configured to search a plurality of evidence sources based at least in part on the search parameter. The search identifies the evidence data. The evidence data is utilized by a clinical decision support system to provide decision support to a healthcare provider for a patient.

BRIEF DESCRIPTION OF SEVERAL VIEWS OF THE DRAWINGS

FIG. 2 illustrates a flow diagram for a method for clinical decision support in accordance with an embodiment of the present invention.

Figure 1:
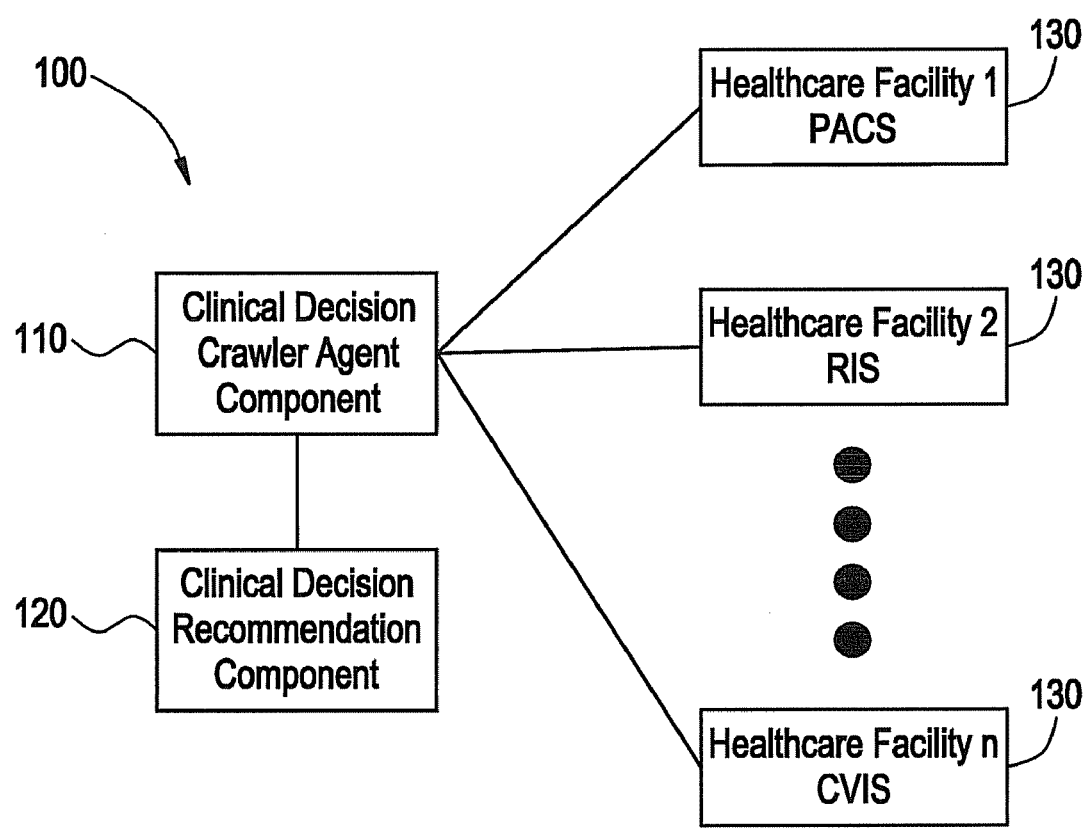
FIG. 1 illustrates a system for clinical decision support in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a system 100 for clinical decision support in accordance with an embodiment of the present invention. The system 100 includes a clinical decision crawler agent component 110, a clinical decision recommendation component 120, and a plurality of evidence sources 130.

The crawler agent component 110 is in communication with the recommendation component 120. The crawler agent component 110 is in communication with the plurality of evidence sources 130. The crawler agent component 110 be in communication with one or more of the plurality of evidence sources 130 utilizing, for example, the Internet, a public telephone network, a dedicated communication line, a virtual private network (VPN), a secure network, and/or an intranet.

In certain embodiments, the recommendation component 120 is not present. In certain embodiments, the recommendation component 120 is integrated with the crawler agent component 110. In certain embodiments, the recommendation component 120 is a separate module in a clinical decision support system.

Evidence sources 130 may include PACS, RIS, CVIS, and/or other medical information management systems located at healthcare facilities, such as hospitals or clinics, for example. Evidence sources 130 may be remote and/or geographically distributed from the system 100. For example, an evidence source 130 may be a PACS at a hospital in another state or country. As another example, an evidence source 130 may be a RIS at a clinic that is part of the same healthcare facility that the system 100 is located at.

In operation, the crawler agent component 110 receives one or more search parameters. The search parameters may be received from a user via a user interface component of a clinical decision support system, for example. It should be noted that a single search parameter may include multiple criteria and/or that criteria may be specified using multiple search parameters.

Search parameters may include, for example, patient name, patient identifier, order number, and exam type. For example, a patient's identifier may be provided to the crawler agent component 110. The crawler agent component 110 may directly use the patient identifier or retrieve additional information from a PACS, RIS, CVIS, or other medical information management system to obtain other patient information such as the patient's name, for example.

Search parameters may include scope information such as, context, domains, countries, and specific evidence sources. That is, a search parameter may include one or more search context limiting criteria. For example, a search parameter may specify a search context of all health care facilities in a particular geographic region.

Search parameters may include genetic information, for example. Genetic information may be used to search for evidence for individuals genetically related to a patient, for example For example, genetic information may include names or identifiers of the patient's parents, siblings, or other relatives. For example, a the names of a patient's parents may be provided to the crawler agent component 110.

The crawler agent component 110 is capable of initiating one or more searches. For example, the crawler agent component 110 may initiate a search at one or more of the plurality of evidence sources 130. A search initiated by the crawler agent component 110 may be based at least in part on the one or more search parameters received by the crawler agent component 110. For example, the crawler agent component 110 may receive a patient's name as a search parameter. In an embodiment, the crawler agent component 110 automatically initiates a search when a search parameter is received. Alternatively, a list of evidence sources to be searched may be provided to a user to select from and/or a user may be prompted to initiate the search of one or more evidence sources. For example, a user may need to provide authentication information, such as a user name and/or password to access certain evidence sources.

The crawler agent component 110 may then initiate a search at one or more evidence sources 130 such as medical information management systems located at the same healthcare facility as the crawler agent 110. As another example, the crawler agent component 110 may be provided a search parameter including a patient identifier and identifiers for the parents of the patient corresponding to the provided patient identifier. The crawler agent component 110 may then determine the patient's name based at least in part on the patient identifier. The crawler agent component 110 may initiate one or more searches of evidence sources 130 based at least in part on one or more of the patient identifier, the patient's name, and the identifiers of the parents of the patient. Alternatively, the crawler agent component 110 may determine the patient's parent's names based at least in part on the identifiers provided and base searches on the patient's parent's names.

A search initiated by the crawler agent component 110 may utilize a protocol such as HL7, DICOM, or XML, for example. For example, the crawler agent component 110 may initiate a search on a PACS at a remote site using a DICOM interface. As another example, the crawler agent component 110 may query a RIS for a patient record and then initiate a DICOM C-FIND operation using a patient name or related study identifiers. The gathering of data may be facilitated using the DICOM protocol, which allows evidence data to be transferred between two or more entities. As another example, evidence may be collected using an XML transfer. As another example, evidence may be searched and/or located using standard Internet search engine algorithms.

In an embodiment, a search parameter received at the crawler agent component 110 may include a context limiter. The context limiter may define the context of a search or searches to be initiated by the crawler agent component 110, for example. As another example, the context limiter may define the domains and/or systems to be searched. For example, the context limiter may specify that the crawler agent component 110 should initiate searches only on systems at the local hospital. As another example, the context limiter may provide a list of PACS and RIS systems to be searched at healthcare facilities in a particular state or geographic area. The list may specify the evidence sources by, for example, Internet Protocol (IP) address, Application Entity (AE) title, or uniform resource locator (URL). As another example, the context limiter may specify a domain such as "all available evidence sources" to be searched by the crawler agent component 110. As another example, the domain may be "all clinics with magnetic resonance imaging (MRI) capabilities."

In an embodiment, the crawler agent component 110 may determine one or more of the evidence sources 130 for initiating a search based at least in part on the context limiter. For example, the context limiter may specify a context of "accessible PACS" and the crawler agent component 110 may then query all known systems for capabilities. Alternatively, the crawler agent component 110 may reference a database or resource list or other data structure, such as a list or table, to determine evidence sources with the capabilities matching the criteria specified in the search parameter. Alternatively, the crawler agent component 110 may be pre-configured with systems matching possible criteria and/or belonging to particular contexts and/or domains. In certain embodiments, the crawler agent component 110 may automatically determine the evidence sources to search. That is, evidence sources to search may be determined without user input beyond the specification of a context limiter. Alternatively, a list of evidence sources meeting the context limiter may be provided to the user to select from. In an embodiment, if no context limiter is provided, the crawler agent component 110 will search all available evidence sources.

Evidence data may be provided by one or more of the evidence sources 130. The evidence data may be provided to the crawler agent component 110, for example. The evidence data may include evidence that meets a search parameter, for example. For example, the evidence data provided by an evidence source 130 may be selected based at least in part on the search initiated by the crawler agent component 110. As another example, an x-ray of a patient may be provided by a remote hospital's PACS when a search is initiated with a parameter including the patient's name. Evidence data may include, for example, prior (e.g., historical) exams and their results, images (e.g., in DICOM format), key image notes, laboratory exams and reports (such as blood work), allergies, pathology results, medication, alerts, document images, and other reports.

In an embodiment, for some or all of the evidence data located by the searches initiated by the crawler agent component 110, a link to the evidence data is provided. That is, the crawler agent component 110 may be adapted to provide a link to evidence data rather than the evidence data itself. The link may be, for example, a URL, path name, or other representation of the location of the evidence data. A link may be provided to a user for review, selection, and/or further searching, before actual evidence data is returned, for example.

In certain embodiments, the system 100 includes a clinical decision recommendation component 120. The recommendation component 120 may be useful for aiding a healthcare practitioner in situations beyond the context of the practitioner's experience, for example. The recommendation component 120 may provide a recommendation. For example, The recommendation may be for a diagnosis and/or course of treatment. For example, the recommendation component 120 may provide a physician with a recommendation for a particular diagnosis.

The recommendation may be based on one or more pieces of evidence. For example, the recommendation component 120 may generate a recommendation based on evidence data. The evidence data and/or a link to the evidence data may be received from and/or provided by the crawler agent component 110, for example. For example, the evidence data utilized by the recommendation component 120 may result from, at least in part, one or more searches initiated by the crawler agent component 110. As is true for a healthcare provider, the recommendation component 120 may provide a better recommendation when more evidence is available to be considered.

Certain embodiments of the present invention may extend beyond the existing context of clinical information systems. Certain embodiments may be employed as clinical evidence search engines as part of a general purpose Internet and/or Web-based search agent and/or diagnosis application.

The components, elements, and/or functionality of system 100 may be implemented alone or in combination in various forms in hardware, firmware, and/or as a set of instructions in software, for example. For example, the crawler agent component may be implemented as a software service running on a PACS. Certain embodiments may be provided as a set of instructions residing on a computer-readable medium, such as a memory or hard disk, for execution on a general purpose computer or other processing device, such as, for example, a PACS workstation or one or more dedicated processors.

FIG. 2 illustrates a flow diagram for a method 200 for clinical decision support in accordance with an embodiment of the present invention. The method 200 includes the following steps, which will be described below in more detail. At step 210, a search parameter is received. At step 220, evidence sources are searched. At step 230, a recommendation is generated. The method 200 is described with reference to elements of systems described above, but it should be understood that other implementations are possible.

At step 210, a search parameter is received. One or more search parameters may be received. The search parameter may be received at a crawler agent component, for example. The crawler agent component may be similar to the crawler agent component 110, described above, for example. The search parameter may be similar to the search parameter received at the crawler agent 110, described above, for example. For example, the search parameter may specify one or more criteria for evidence data to be searched for. A search parameter may include criteria such as patient name, patient identifier, context limiters, domains, and/or genetic information. In an embodiment, more than one search parameter may be received.

At step 220, evidence sources are searched. The evidence sources to be searched may be similar to the evidence sources 130, described above, for example. One or more of the evidence sources may be searched when a search is initiated at the evidence source. The search may be initiated by crawler agent component, for example. The crawler agent component may be similar to the crawler agent component 110, described above, for example.

The search may be based at least in part on a search parameter. For example, the search may be based on a search parameter including a patient's name. The search parameter may be similar to the search parameter received at step 210, described above, for example. In an embodiment, the search is based on a search parameter received at crawler agent component 110. In an embodiment, an evidence source may be searched based on more than one search parameter. For example, an evidence source such as a RIS system at a hospital in another state may be searched based on a patient's name and the patient's address. Alternatively, the patient's name and address may be a single search parameter.

The search of one more evidence sources may identify evidence data. For example, the search of a clinic's RIS for a patient's name may return a series of DICOM images and key image notes for an exam the patient had performed at the clinic. The evidence data may be provided to a crawler agent component, for example. In an embodiment, a link to the evidence data may be provided.

At step 230, a recommendation is generated. The recommendation may be a recommendation for a course of treatment and/or a diagnosis, for example. The recommendation may be generated by a recommendation component. The recommendation component may be similar to the recommendation component 120, described above, for example.

The recommendation may be based at least in part on evidence data. The evidence data may include evidence data provided by the search of evidence sources, for example. The search of evidence sources may be similar to the search of evidence sources at step 220, described above, for example. Evidence data may include evidence provided by a user, for example. For example, the recommendation component 120 may generate a recommendation based on evidence data including evidence provided by a search initiated by crawler agent component 110 and a user. As another example, the recommendation may be generated based on links to evidence data provided by crawler agent 110.

In certain embodiments, at least one of the plurality of evidence sources to be searched is selected or determined based at least in part on a search parameter. In an embodiment, an evidence source to be search is determined automatically. For example, the crawler agent component 110 may automatically determine the evidence sources to search. That is, evidence sources to search may be determined without user input beyond the specification of a context limiter. Alternatively, a list of evidence sources meeting the context limiter may be provided to the user to select from. In an embodiment, if no context limiter is provided, plurality of evidence sources to be searched will include all available evidence sources.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide a system and method for a clinical decision crawler agent. Further, certain embodiments of the present invention provide for a clinical decision support system that is adapted to make a recommendation based on evidence obtained by the clinical decision crawler agent. Certain embodiments provide a technical effect of locating and obtaining evidence from multiple evidence sources. Certain embodiments provide a technical effect of providing a recommendation based on evidence located by a clinical decision crawler agent.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A clinical decision support system including:
   a processor:
   a computer-readable medium encoded with a crawler agent component,
      wherein the crawler agent component receives a search parameter, wherein the search parameter specifies a criteria for evidence data to be searched for, wherein the search parameter includes a context limiter, and
      wherein the crawler agent component initiates a simultaneous search of a plurality of evidence sources based at least in part on the search parameter, wherein the search identifies the evidence data, wherein the evidence data is utilized by the clinical decision support system to provide decision support to a healthcare provider for a patient, wherein at least one of the plurality of evidence sources is selected based at least in part on the context limiter, the context limiter restricting evidence to be searched for to an area in which at least one healthcare facility is located and/or healthcare facility capabilities;
      wherein the crawler agent component provides a link to the source of the evidence data, wherein each of the plurality of evidence sources comprises one or more of PACS, RIS, and/or CVIS, wherein the search parameter comprises one or more of patient name, patient identifier, order number and/or exam type, and wherein the evidence data comprises one or more of prior exams, images, key image notes, laboratory exams and reports, allergies, pathology results, medication, alerts, and/or document images, and
   a recommendation component that generates a recommendation for a diagnosis and/or course of treatment for a patient based at least in part on the evidence data.

2. The system of claim 1, wherein the search parameter includes an identifier for a genetic relative of the patient.

3. The system of claim 1, wherein the context limiter is a domain.

4. The system of claim 1, wherein the crawler agent component automatically determines a domain to search.

5. The system of claim 4, wherein the domain is based at least in part on the search parameter.

6. The system of claim 1, wherein the crawler agent component automatically initiates a search when the search parameter is received.

7. The system of claim 1, wherein the crawler agent component is located at a first healthcare facility and wherein at least one of the plurality of evidence sources is located at a second healthcare facility, wherein the second healthcare facility is geographically remote from the first healthcare facility.

8. A method for clinical decision support, the method including:
   receiving a search parameter at a crawler agent component, wherein the search parameter specifies a criteria for evidence data to be searched for, wherein the search parameter includes a context limiter that restricts evidence data to be searched for to an area in which at least one healthcare facility is located and/or healthcare facility capabilities;

simultaneously searching of a plurality of evidence sources based at least in part on the search parameter, wherein the search identifies the evidence data, wherein the evidence data is utilized by a clinical decision support system to provide decision support to a healthcare provider for a patient, wherein each of the plurality of evidence sources comprises one or more of PACS, RIS, and/or CVIS, wherein the search parameter comprises one or more of patient name, patient identifier, order number and/or exam type, and wherein the evidence data comprises one or more of prior exams, images, key image notes, laboratory exams and reports, allergies, pathology results, medication, alerts, and/or document images;

providing a link to the evidence data; and automatically generating a diagnostic and/or treatment recommendation for the patient based at least in part on the evidence data.

9. The method of claim 8, wherein the search parameter includes an identifier for a genetic relative of the patient.

10. The method of claim 8, further including automatically selecting at least one of the plurality of evidence sources based at least in part on the search parameter.

11. A computer-readable medium including a set of instructions for execution on a computer, the set of instructions including:

a search parameter receiving routine that receives a search parameter, wherein the search parameter specifies a criteria for evidence data to be searched for, wherein at least one of a plurality of evidence sources is selected based at least in part on a context limiter, the context limiter restricting evidence to be searched for to an area in which at least one healthcare facility is located and/or healthcare facility capabilities;

a search routine that simultaneously searches a plurality of evidence sources based at least in part on the search parameter, wherein the search identifies the evidence data, wherein the evidence data is utilized by a clinical decision support system to provide decision support to a healthcare provider for a patient, wherein each of the plurality of evidence sources comprises one or more of PACS, RIS, and/or CVIS, wherein the search parameter comprises one or more of patient name, patient identifier, order number and/or exam type, and wherein the evidence data comprises prior exams, images, key image notes, laboratory exams and reports, allergies, pathology results, medication, alerts, and/or document images;

a link-providing routine that provides a link to the evidence data; and a recommendation generation routine that generates a diagnostic and/or treatment recommendation for the patient based at least in part on the evidence data.

12. The set of instructions of claim 11, further including a search determination routine that automatically selects at least one of the plurality of evidence sources based at least in part on the search parameter.

* * * * *